US009642371B2

(12) United States Patent
Jelesko et al.

(10) Patent No.: US 9,642,371 B2
(45) Date of Patent: May 9, 2017

(54) COMPOSITIONS AND METHODS COMPRISING COLLETOTRICHUM FOR CONTROLLING PLANT SPECIES

(71) Applicants: John G. Jelesko, Blacksburg, VA (US); Matthew Kasson, Christiansburg, VA (US)

(72) Inventors: John G. Jelesko, Blacksburg, VA (US); Matthew Kasson, Christiansburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 14/528,188

(22) Filed: Oct. 30, 2014

(65) Prior Publication Data

US 2015/0119246 A1 Apr. 30, 2015

Related U.S. Application Data

(60) Provisional application No. 61/897,365, filed on Oct. 30, 2013.

(51) Int. Cl.
*A01N 63/00* (2006.01)
*A01N 63/04* (2006.01)

(52) U.S. Cl.
CPC .................................... *A01N 63/04* (2013.01)

(58) Field of Classification Search
None
See application file for complete search history.

(56) References Cited

U.S. PATENT DOCUMENTS

| | | | | |
|---|---|---|---|---|
| 4,715,881 | A | 12/1987 | Andersen et al. | |
| 4,775,405 | A * | 10/1988 | Caulder ................. | A01N 63/04 504/117 |
| 4,808,207 | A | 2/1989 | Gotlieb et al. | |
| 5,221,314 | A | 6/1993 | Watson et al. | |
| 2008/0269177 | A1 | 10/2008 | Bessette | |

FOREIGN PATENT DOCUMENTS

| | | |
|---|---|---|
| CN | 101919412 | 7/2012 |
| CN | 101919412 B | 7/2012 |

OTHER PUBLICATIONS

By Ivic et al.(Identification of Colletotrichum Species Causing Bitter Rot of Apple and pear in Croatia, J. of Phytopathology, 2013, 161(4), 284-6).ABS.*
Benhase, E. and Jelesko, J., "Germinating and culturing axenic poison ivy seedlings." HortScience 48(12), pp. 1525-1529, 2013.
Damm et al., "The Colletotrichum acutatum species complex." Studies in Mycology 73, pp. 37-113, 2012.
Freeman, S. and Katan, T., "Identification of Colletotrichum species responsible for anthracnose and root necrosis of strawberry in Israel." Phytopathology, vol. 87, No. 5, pp. 516-521, 1997.
Inderbitzin P, Davis RM, Bostock RM, Subbarao KV, "The Ascomycete Verticillium longisporum is a Hybrid and a Plant Pathogen with an Expanded Host Range." PLoS ONE 6(3): Mar. 2011, 13 pages.
M. T. Kasson, J. R. Pollok, E. B. Benhase, and J. G. Jelesko, Department of Plant Pathology, Physiology, and Weed Science, Virginia Tech, Blacksburg, VA, "First Report of Seedling Blight of Eastern Poison Ivy (*Toxicodendron radicans*) by Colletotrichum fioriniae in Virginia," Plant Disease Journal, 98(7): 995, 2014.
Marcelino et al., "Host plant associations of an entomopathogenic variety of the fungus, Colletotrichum acutatum, recovered from the elongate hemlock scale, Fiorinia externa." Journal of Insect Science, vol. 9, Article 25, 11 pages, 2009.
Puoci et al., "Polymer in agriculture: a review." American Journal of Agricultural and Biological Sciences 3(1), pp. 299-314, 2008.
S. Freeman, "Management, Survival Strategies, and Host Range of Colletotrichum acutatum on Strawberry," HortScience vol. 43(1), pp. 66-68, 2008.
Shivas, R.G. and Tan, Y.P., "A taxonomic re-assessment of Colletotrichum acutatum, introducing *C. fioriniae* comb. et. stat. nov. and *C. simmondsii* sp. nov." Fungal Diversity 39, pp. 111-122, 2009.
Woudenberg et al., "Multiple Didymella teleomorphs are linked to the Phoma clematidina morphotype." Persoonia 22, pp. 56-62, 2009.

* cited by examiner

*Primary Examiner* — Alton Pryor
(74) *Attorney, Agent, or Firm* — New River Valley IP Law, PC; Michele L. Mayberry

(57) ABSTRACT

Provided are methods and compositions for controlling at least one plant. Methods and compositions can comprise at least one strain of *Colletotrichum* spp., such as *Colletotrichum fioriniae* TR-123, *Colletotrichum fioriniae* TR-126, and combinations thereof. Methods and compositions of the invention are useful, for example, for controlling *Toxicodendron radicans* and/or *Schinus terebinthifolus*.

19 Claims, 3 Drawing Sheets

Disease progression among treatments on poison-ivy. Treatments with significantly different Area Under the Disease Progress Curve means are indicated by different letters, as determined by ANOVA with Tukey's mean comparisons using Minitab 16.1.0. Disease ratings were: 1 = healthy, 2 = chlorotic leaves, 3 = wilt/necrosis, and 4 = dead.

A, Three week-old poison-ivy seedling inoculated with a sterile agar plug at base (negative control), B, *C. fioriniae* isolate TR-126, C-F, *C. fioriniae* infected plants: C-E, wilt symptoms, E, orange acervuli on cotyledon and endocarp (see insert), F, chlorophyll loss and light orange acervuli on cotyledons (see insert).

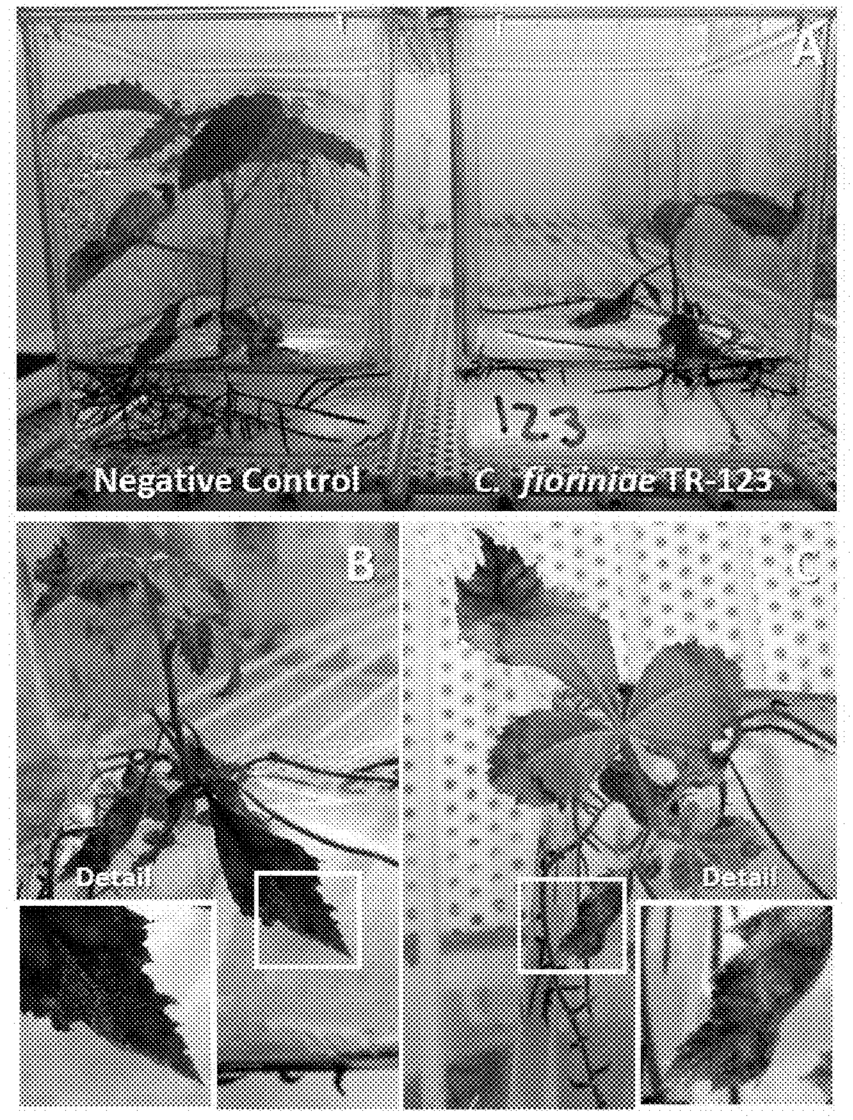

A, Four week old Brazilian peppertree (*Schinus terebinthifolius*) seedlings inoculated with a sterile agar plug (negative control, left) and *C. fioriniae* isolate TR-123 (right) at base of seedling, B-C *C. fioriniae* isolate TR-123 infected plants: B, wilt symptoms and leaf blight, B-C, leaf tip discoloration and necrosis on green terminal leaves, B-C, orange acervuli of *C. fioriniae* on necrotic leaves (see insert).

FIGS. 3A-3C

COMPOSITIONS AND METHODS COMPRISING COLLETOTRICHUM FOR CONTROLLING PLANT SPECIES

CROSS-REFERENCE TO RELATED APPLICATIONS

The present application relies on the disclosure of and claims priority to and the benefit of the filing date of U.S. Provisional Application No. 61/897,365, filed Oct. 30, 2013, the disclosure of which is hereby incorporated by reference herein in its entirety.

REFERENCE TO SEQUENCE LISTING IN COMPUTER READABLE FORM

The present application contains a Sequence Listing. A copy of the Sequence Listing has been submitted in ASCII format via EFS-Web and is hereby incorporated by reference herein in its entirety. The ASCII file is named VTIP91-Sequence-Listing-Replacement ST25.txt, is dated Nov. 12, 2014, is 4.23 kilobytes in size, and is identical to the paper copy filed on Nov. 12, 2014.

FIELD OF THE INVENTION

Disclosed herein are compositions comprising at least one strain of *Colletotrichum* spp. for controlling plant species, such as undesirable plant species (e.g., *Toxicodendron radicans*, or "poison ivy"). Further disclosed are methods of using such compositions for controlling plant species in various environments.

BACKGROUND OF THE INVENTION

Many important environments contain a substantial population of undesirable plant species. These undesirable plant species are a nuisance in human-controlled environments, in particular landscaped urban and suburban settings, as well as managed parklands.

Moreover, undesirable plant species can contribute to mammalian infection as well. Many outdoor areas receive high traffic from humans and their pet companions. Often, while enjoying the outdoors or performing landscaping work, undesirable plant species, such as poison ivy for example, cause allergic reactions in humans and domestic animals resulting in rashes where the undesirable plant contacted the skin. These rashes become highly inflamed and cause severe itching. As animals scratch the inflamed area, the skin can become infected by bacteria and result in the need for antibiotic intervention. Further still, these undesirable plant species can cause an appearance that observers find unattractive, especially in gardens that are maintained for aesthetic appeal.

Currently, the most common approach to combating undesirable plants is to use chemical herbicides. Use of chemical herbicides, however, is not without its challenges. Due to increases in herbicide use, many undesirable plants have developed herbicide resistance. The resistant plants will often need to be treated with newer herbicides, while other undesirable plants need to be treated with a completely different herbicide. Such practices increase herbicide resistance and typically require the continuous retreatment of land. This not only increases the overall cost of treatment but also increases the potential for toxic accumulation of the herbicide in the environment and in soils. Thus, there is a continuing need for newer, environmentally superior solutions for controlling undesirable plant species.

Microbial solutions have been developed for use as an alternative, or in some cases as a supplement, to chemical herbicides. Exemplary treatment compositions can be found in U.S. Pat. Nos. 4,775,405; 4,715,881; 4,808,207; and 5,221,314, as well as U.S. Patent Application Publication No.: 2008/0269177 and CN Patent No.: 101919412. Microbial solutions typically involve use of a living organism (e.g., bacteria and fungi) that is capable of controlling (e.g., killing and/or intervening in the life cycle) of the undesirable plant. Examples of microbial solutions for controlling undesirable plants include microbial herbicides, and in particular, fungal herbicides including strains of *Colletotrichum* spp.

As natural agents, microbial solutions to pest management offer more eco-friendly options for controlling undesirable plants. A need exists for superior microbial control of noxious weedy/invasive plant pests.

SUMMARY OF THE INVENTION

*Colletotrichum fioriniae* is a member of the large cosmopolitan *C. acutatum* species complex. (Damm, U. et al., Stud. Mycol., 73:37, 2012). Known agricultural hosts of *C. acutatum* include apple, European blueberry, grape, olive, papaya, and strawberry. (Damm, U. et al., Stud. Mycol., 73:37, 2012). The life history of *C. fioriniae* ranges from an epizootic of certain scale insect populations to an endophyte of plants. (Marcelino, J. et al., J. Insect Sci., 9:25, 2009; Shivas, R. et al., Fungal Divers., 39:111). The present disclosure extends the phytopathology of *C. fioriniae* to include noxious weedy plants, such as poison ivy or the Brazilian pepper tree, which are typically undesirable.

Disclosed herein are compositions which offer an improved microbial herbicide for controlling plant species, such as undesirable plant species. The composition can comprise an agronomically suitable carrier, and a fungal strain of *Colletotrichum* spp., in particular embodiments, *Colletotrichum fioriniae*. In an embodiment, additional optional ingredients (e.g., beneficial microbes, herbicides, pesticides, fungicides, nematicides, and combinations thereof) may also be used in combination with the compositions described herein, including as part of the same composition or applied as a separate treatment.

Disclosed herein are also methods for controlling plants, such as undesirable plants. In an embodiment, the method comprises contacting an undesirable plant or plant part with a strain of *Colletotrichum* spp. (e.g., *Colletotrichum fioriniae*) or compositions described herein which comprise a strain of *Colletotrichum* spp. (e.g., *Colletotrichum fioriniae*). In another embodiment, the method comprises contacting a soil with a strain of *Colletotrichum* spp. (e.g., *Colletotrichum fioriniae*) or compositions described herein which comprise a strain of *Colletotrichum* spp. (e.g., *Colletotrichum fioriniae*).

BRIEF DESCRIPTION OF THE DRAWINGS

FIGS. 3A-3C are photos showing the effect of *Colletotrichum fioriniae* treatments on *Schinus terebinthifolus* (i.e., Brazilian Pepper Tree) according to methods described herein.

DETAILED DESCRIPTION OF THE INVENTION

Figure 1:
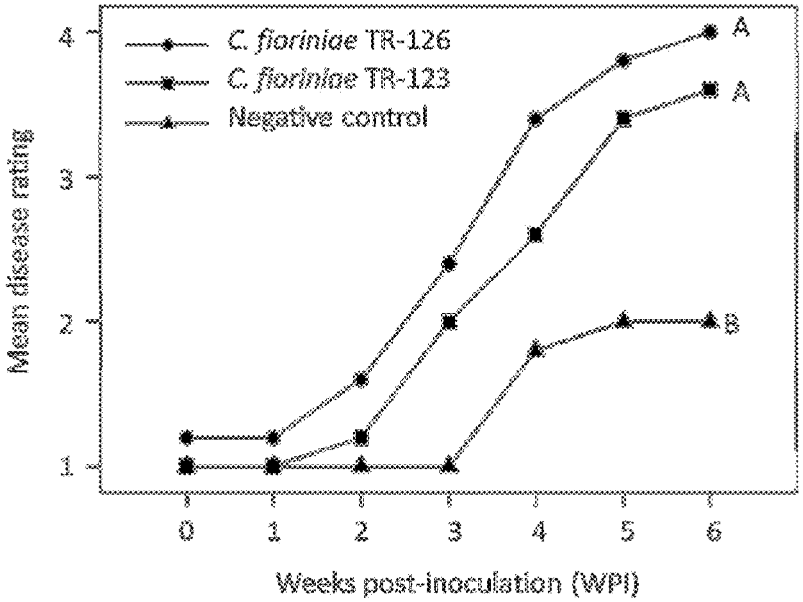
FIG. 1 is a graph illustrating the effect of *Colletotrichum fioriniae* treatments on poison-ivy according to methods described herein.
Figures 2A, 2B, 2C, 2D, 2E, 2F:
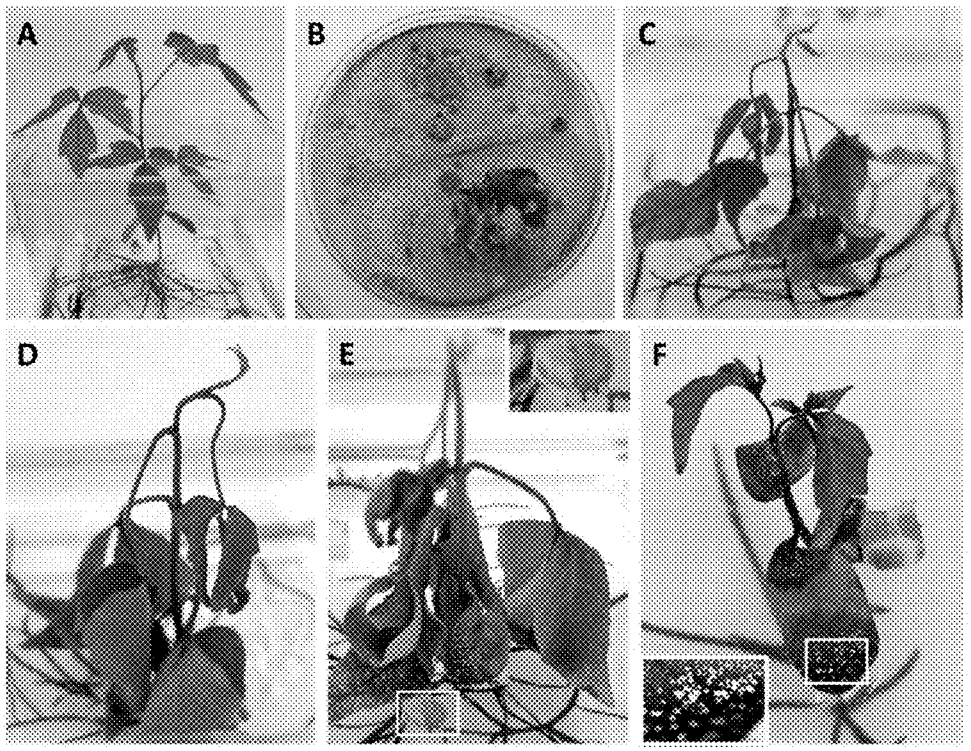
FIGS. 2A-2F are photos showing the effect of *Colletotrichum fioriniae* treatments on *Toxicodendron radicans* (i.e., Poison Ivy) according to methods described herein.

The disclosed embodiments relate to compositions and methods for controlling infestations of arthropod pests, particularly infestations of bed bugs in human dwellings.

DEFINITIONS

As used herein, the term "carrier" means an "agronomically or agriculturally acceptable carrier." An "agronomically or agriculturally acceptable carrier" means any material which can be used to deliver the actives (e.g., microorganism(s) described herein, etc.) to a plant or plant part (e.g., plant foliage, plant roots, etc.) for control of the plant, and preferably which carrier can be applied to the plant or plant part with minimal adverse effect or without having an adverse effect on the growth of other non-targent plants, soil structure, soil drainage or the like. As used herein, the term "soil-compatible carrier" means any agronomically acceptable carrier which can be added to a soil with minimal adverse effect or without causing/having an adverse effect on desirable plant growth, soil structure, soil drainage, or the like. As used herein, the term "foliar-compatible carrier" means any agronomically acceptable carrier which can be added to the foliage (e.g. leaves, etc.) of an undesirable plant or plant part with minimal adverse effect or without causing/having an adverse effect on a desirable plant, plant part, plant growth, plant health, or the like.

As used herein, the term "agronomically beneficial ingredient(s)" or "agriculturally beneficial ingredient(s)" means any agent or combination of agents capable of causing or providing a beneficial and/or useful effect in agriculture, horticulture, and/or agronomy.

As used herein, the term "beneficial microorganism(s)", "beneficial microbe(s)", "beneficial bacterium/bacteria", "beneficial fungus/fungi" etc., means any microorganism (e.g., bacteria, fungus, etc., or combinations thereof) having one or more properties (e.g., herbicidal activity, fungicidal activity, insecticidal activity) beneficial to growing plants that can be used to target undesirable species.

As used herein, the term "biostimulant(s)" means any agent or combination of agents capable of enhancing metabolic or physiological processes within plants and soils.

As used herein, the term "composition(s)" has its art recognized meaning and means a material composition that comprises at least two components (e.g., a microorganism, a carrier, etc.). The compositions disclosed herein may be further formulated to practice one or more of the methods described herein.

As used herein, the term "control" or "controlling" as in e.g., the phrase: the "control" of at least one plant, or as in the phrase: "controlling at least one plant", means preventing, reducing, killing, inhibiting the growth of, inhibiting the reproduction of, and/or eliminating at least one plant. Indeed, "control" or "controlling" as used herein refers to any indicia of success in prevention, killing, inhibition, elimination, reduction or amelioration of at least one plant.

As used herein the term "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or culture broth, suspension or medium used to culture or grow said organism. A compound "derived from" or "obtainable from" means that a compound may be isolated from or produced by a cell culture, whole cell broth, suspension, filtrate, supernatant, fraction or extract.

As used herein, the terms "effective amount", "effective concentration", or "effective dosage" means the amount, concentration, or dosage of at least one active ingredient (e.g., at least one microorganism or a supernatant, filtrate, or extract derived from the at least one microorganism, suspension or whole cell broth; at least one herbicide; etc.) sufficient for controlling at least one plant. The actual effective dosage in absolute value depends on factors including, but not limited to, synergistic or antagonistic interactions between the other active or inert ingredients which may enhance or reduce the controlling effects of the at least one active ingredient and/or the stability of the at least one active ingredient in compositions and/or formulations as plant treatments. The "effective amount", "effective concentration", or "effective dosage" of the at least one active ingredient may be determined, e.g., by a routine dose response experiment.

As used herein, the term "extract" means liquid substance removed from cells by a solvent (e.g., water, detergent, buffer, organic solvent) and separated from the cells by centrifugation, filtration or other method.

As used herein, the term "filtrate" means liquid from a whole broth culture that has passed through a membrane.

As used herein, the term "foliage" means any part or organ of a plant above the ground. Non-limiting examples include leaves, needles, stalks, stems, flowers, fruit bodies, fruits, etc. As used herein, the term "foliar application", "foliarly applied", and variations thereof, is intended to include application of an active ingredient to the foliage or above ground portions of the plant, (e.g., the leaves of the plant). Application may be effected by any means known in the art (e.g., spraying the active ingredient).

As used herein, the term "formulation(s)" means a product comprising specified ingredients in predetermined amounts or proportions, as well as any product that results, directly or indirectly, from combining specified ingredients in specified amounts.

As used herein, the term "herbicide" or "herbicidal means any agent or combination of agents (e.g., at least one microorganism, at least one chemical, etc.) capable of being toxic to a plant (e.g., a weed such as poison ivy, etc.), controlling a plant, killing a plant, inhibiting the growth of a plant, and/or inhibiting the reproduction of a plant.

As used herein, the term "inoculum" means any form of microbial cells, or spores, which are capable of propagating on or in a substrate (e.g., a soil, a plant or plant part, etc.) when the conditions of temperature, moisture, etc., are favorable for microbial growth.

As used herein, the terms "isolated" or "isolated compound" means essentially free of other compounds or substances, e.g., at least about 20% pure, preferably at least about 40% pure, more preferably about 60% pure, even more preferably about 80% pure, most preferably about 90% pure, and even most preferably about 99% pure, as determined by analytical methods, including but not limited to chromatographic methods, electrophoretic methods. A compound "derived from" a *Colletotrichum* species also encompasses a metabolite.

As used herein, the term "metabolite" means a compound, substance or byproduct of a fermentation of a microorganism, or supernatant, filtrate, or extract obtained from a microorganism that has pesticidal activity.

As used herein, the term "nutrient(s)" means any nutrient (e.g., vitamins, macrominerals, micronutrients, trace minerals, organic acids, etc.) which are needed for plant growth, plant health, and/or plant development.

As used herein, the terms "plant(s)" and "plant part(s)" means all plants and plant populations including both desired and undesired plants (e.g., wild plants, crop plants, etc.). Plants may be obtained by conventional plant breeding and optimization methods or by biotechnological and genetic engineering methods or by combinations of these methods, including the transgenic plants and including the plant cultivars protectable or not protectable by plant breeders' rights. As used herein, the terms "plant part" or "plant parts" are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material and vegetative and generative propagation material (e.g., cuttings, tubers, rhizomes, offshoots and seeds, etc.).

As used herein, the terms "spore", "microbial spore", etc., has its normal meaning which is well known and understood by those of skill in the art. As used herein, the terms "spore" and "microbial spore" mean a microorganism in its dormant, protected state.

As used herein, the term "supernatant" means the liquid remaining when cells are grown in broth or harvested in liquid from an agar plate and are removed by centrifugation, filtration, sedimentation, or other means well known in the art.

As used herein, the term "undesirable plant(s)" means any plant targeted for treatment with a composition, method, or fungal herbicide of the invention. Target plants can be nuisance, unwanted, noxious, weedy, invasive, or harmful plant or vegetation (e.g., harmful to animals, harmful to ornamental plants, crops, etc.). The term "desirable plant(s)" means any plant that is not a target for such treatment or that may benefit from target undesirable plants being controlled or eliminated.

As used herein, the terms "whole broth culture" or "whole cell broth" mean a liquid culture containing both cells and media. If bacteria are grown on a plate, the cells can be harvested in water or other liquid, whole culture. The terms "whole broth culture" and "whole cell broth" are used interchangeably.

Microorganisims

In one embodiment, the at least one microorganism described herein is at least one strain comprising herbicidal activity (i.e., a microbial herbicide). In a particular aspect, the microbial herbicide is at least one fungal herbicide, at least one bacterial herbicide, or combinations thereof.

In a more particular aspect, the at least one fungal herbicide is a strain of *Colletotrichum* spp. In an even more particular aspect, the fungal herbicide is a strain of *Colletotrichum* spp. chosen from at least one of *Colletotrichum acutatum, Colletotrichum agaves, Colletotrichum alcornii, Colletotrichum arachidis, Colletotrichum baltimorense, Colletotrichum capsici, Colletotrichum caudatum, Colletotrichum cereale, Colletotrichum coccodes, Colletotrichum crassipes, Colletotrichum dematium, Colletotrichum derridis, Colletotrichum destructivum, Colletotrichum falcatum, Colletotrichum fioriniae, Colletotrichum fragariae, Colletotrichum gloeosporioides, Colletotrichum gossypii, Colletotrichum graminicola, Colletotrichum hanaui, Colletotrichum higginsianum, Colletotrichum jacksonii, Colletotrichum kahawae, Colletotrichum lindemuthianum, Colletotrichum lini, Colletotrichum mangenotii, Colletotrichum musae, Colletotrichum navitas, Colletotrichum nicholsonii, Colletotrichum nigrum, Colletotrichum orbiculare, Colletotrichum paspali, Colletotrichum pisi, Colletotrichum somersetense, Colletotrichum sublineolum, Colletotrichum trichellum, Colletotrichum trifolii, Colletotrichum truncatum, Colletotrichum viniferum, Colletotrichum zoysiae*, or combinations thereof.

In still an even more particular embodiment, the fungal herbicide is at least one strain of *Colletotrichum fioriniae*. In a particular aspect, the at least one strain of *Colletotrichum fioriniae* is chosen from at least one of *Colletotrichum fioriniae* strain TR-123, *Colletotrichum fioriniae* strain TR-126, and combinations thereof. In another aspect, the at least one strain of *Colletotrichum fioriniae* is *Colletotrichum fioriniae* strain TR-123. In still another aspect, the at least one strain of *Colletotrichum* fioriniae is *Colletotrichum fioriniae* strain TR-126. In still yet another aspect, the at least one strain of *Colletotrichum fioriniae* is a mixture (e.g., a blend) of *Colletotrichum fioriniae* strain TR-123 and *Colletotrichum fioriniae* strain TR-126.

The strains of *Colletotrichum* spp. described herein, and in particular, strains of *Colletotrichum fioriniae* and variants thereof, can be cultivated in nutrient medium using methods known in the art. Suitable media may be available from commercial sources or prepared according to published compositions. Non-limiting examples of acceptable growth media include blood agar plates, Mathur's medium (Freeman, S., Katan, T., Phytopathology, 87: 516-521, 2013), acidified potato dextrose agar (APDA), oatmeal agar (OA), potato dextrose agar, tryptic soy medium, yeast extract mannitol medium (YEM), glycerol yeast extract (GYEA), yeast extract-peptone-glycerol (YPG), peptone yeast extract glucose (PYG) MacConkey agar, or malt extract agar, or in flasks containing suitable liquid media such as tryptic soy broth, YEM broth, KMB broth, GYEA broth. YPG broth, PYG broth, Czapek-Dox medium, potato dextrose broth etc.

The organisms may be cultivated by shake flask cultivation, small scale or large scale fermentation (including but not limited to continuous, batch, fed-batch, or solid state fermentations) in laboratory or industrial fermenters performed in suitable medium and under conditions allowing cell growth. The cultivation may take place in suitable nutrient medium comprising carbon and nitrogen sources and inorganic salts, using procedures known in the art. For long-term storage, isolates were grown on glass microfiber filters (whatman, dried in individual envelopes, and stored at −22° C. These culture methods may be used in the preparation of an inoculum of *Colletotrichum* spp. for application to a carrier to be applied to undesired plants, plant parts, or soils having at least one undesired plant.

Compositions:

Compositions used in embodiments disclosed herein can comprise at least one agronomically suitable carrier and at least one strain of *Colletotrichum* spp. or a suspension or a whole cell broth comprising at least one strain of *Colletotrichum* spp., or a supernatant, filtrate, or extract derived from the at least one strain of *Colletotrichum* spp, suspension, or whole cell broth.

In particular aspects the compositions described herein comprise at least one agronomically suitable carrier and at least one strain of *Colletotrichum* spp. selected from the group consisting of *Colletotrichum acutatum, Colletotri-*

*chum agaves, Colletotrichum alcornii, Colletotrichum arachidis, Colletotrichum baltimorense, Colletotrichum capsici, Colletotrichum caudatum, Colletotrichum cereale, Colletotrichum coccodes, Colletotrichum crassipes, Colletotrichum dematium, Colletotrichum derridis, Colletotrichum destructivum, Colletotrichum falcatum, Colletotrichum fioriniae, Colletotrichum fragariae, Colletotrichum gloeosporioides, Colletotrichum gossypii, Colletotrichum graminicola, Colletotrichum hanaui, Colletotrichum higginsianum, Colletotrichum jacksonii, Colletotrichum kahawae, Colletotrichum lindemuthianum, Colletotrichum lini, Colletotrichum mangenotii, Colletotrichum musae, Colletotrichum navitas, Colletotrichum nicholsonii, Colletotrichum nigrum, Colletotrichum orbiculare, Colletotrichum paspali, Colletotrichum pisi, Colletotrichum somersetense, Colletotrichum sublineolum, Colletotrichum trichellum, Colletotrichum trifolii, Colletotrichum truncatum, Colletotrichum viniferum, Colletotrichum zoysiae*, or combinations thereof.

In a more particular embodiment, compositions described herein can comprise at least one agronomically suitable carrier and at least one strain of *Colletotrichum fioriniae*. In a particular aspect, the at least one strain of *Colletotrichum fioriniae* is selected from the group consisting of *Colletotrichum fioriniae* strain TR-123, *Colletotrichum fioriniae* strain TR-126, and combinations thereof. In an aspect, the at least one strain of *Colletotrichum fioriniae* is *Colletotrichum fioriniae* strain TR-123. In another aspect, the at least one strain of *Colletotrichum fioriniae* is *Colletotrichum fioriniae* strain TR-126. In still another aspect, the at least one strain of *Colletotrichum fioriniae* is a combination of *Colletotrichum fioriniae* strain TR-123 and *Colletotrichum fioriniae* strain TR-126.

In a particular embodiment, compositions can comprise at least one agronomically suitable carrier and whole broth cultures, liquid cultures, or suspensions of a strain from a *Colletotrichum* spp., e.g., a strain having the identifying characteristics of *Colletotrichum fioriniae*, as well as supernatants, filtrates or extracts obtained from a strain of a *Colletotrichum fioriniae*., e.g., one or more metabolites or isolated compounds derived from a strain of a *Colletotrichum fioriniae* or combinations of the foregoing which in particular have herbicidal activity.

Compositions described herein typically have the benefit of controlling at least one plant, especially at least one undesirable plant, such as plants from the genus *Toxicodendron* spp. and *Schinus* spp.

In a particular aspect, the compositions described herein will have the benefit of controlling at least one of *Toxicodendron acuminatum, Toxicodendron diversilobum* (i.e., Western poison oak), *Toxicodendron orientale* (i.e., Asian poison ivy), *Toxicodendron parviflorum, Toxicodendron potaninii* (i.e., Potanin's lacquer tree, also referred to as the Chinese varnish tree), *Toxicodendron pubescens* (i.e., Atlantic poison oak), *Toxicodendron radicans* (i.e., Poison ivy), *Toxicodendron rydbergii* (i.e., Western poison ivy), *Toxicodendron striatum* (i.e., Manzanillo), *Toxicodendron succedaneum* (i.e., Wax tree), *Toxicodendron sylvestre, Toxicodendron vernicifluum* (i.e., Japanese lacquer tree or Japanese varnish tree), *Toxicodendron vernix* (i.e., Poison sumac), *Schinus engleri, Schinus latifolius, Schinus lentiscifolius, Schinus molle* (i.e., Peruvian Pepper Tree), *Schinus pearcei, Schinus polygamus, Schinus terebinthifolius* (i.e., Brazilian Pepper Tree, also referred to as Aroeira, Rose Pepper, and Christmasberry), *Schinus, venture*, and *Schinus weinmanniifolius.*

In still a more particular aspect, the compositions described herein will have the benefit of controlling *Toxicodendron diversilobum* (i.e., Western poison oak). In still yet a more particular aspect, the compositions described herein will have the benefit of controlling *Toxicodendron pubescens* (i.e., Atlantic poison oak). In still an even more particular aspect, the compositions described herein will have the benefit of controlling *Toxicodendron radicans* (i.e., Poison ivy). In still another particular aspect, the compositions described herein will have the benefit of controlling *Toxicodendron rydbergii* (i.e., Western poison ivy). In still yet another particular aspect, the compositions described herein will have the benefit of controlling *Toxicodendron vernix* (i.e., Poison sumac). In still another particular aspect, the compositions described herein will have the benefit of controlling the noxious and invasive *Schinus terebinthifolius* (otherwise referred to as Brazilian pepper tree, aroeira, rose pepper, and Christmasberry).

The compositions described herein can be of any form so long as the composition is able to support the desired activity (effective amount) of the microorganism disclosed here in (i.e., the at least one strain of *Colletotrichum* spp., e.g., *Colletotrichum acutatum, Colletotrichum agaves, Colletotrichum alcornii, Colletotrichum arachidis, Colletotrichum baltimorense, Colletotrichum capsici, Colletotrichum caudatum, Colletotrichum cereale, Colletotrichum coccodes, Colletotrichum crassipes, Colletotrichum dematium, Colletotrichum derridis, Colletotrichum destructivum, Colletotrichum falcatum, Colletotrichum fioriniae, Colletotrichum fragariae, Colletotrichum gloeosporioides, Colletotrichum gossypii, Colletotrichum graminicola, Colletotrichum hanaui, Colletotrichum higginsianum, Colletotrichum jacksonii, Colletotrichum kahawae, Colletotrichum lindemuthianum, Colletotrichum lini, Colletotrichum mangenotii, Colletotrichum musae, Colletotrichum navitas, Colletotrichum nicholsonii, Colletotrichum nigrum, Colletotrichum orbiculare, Colletotrichum paspali, Colletotrichum pisi, Colletotrichum somersetense, Colletotrichum sublineolum, Colletotrichum trichellum, Colletotrichum trifolii, Colletotrichum truncatum, Colletotrichum viniferum, Colletotrichum zoysiae*, and in particular aspects, at least one strain of *Colletotrichum fioriniae*, and in more particular aspects at least one strain of *Colletotrichum fioriniae* selected from the group consisting of *Colletotrichum fioriniae* strain TR-123, *Colletotrichum fioriniae* strain TR-126, and combinations thereof), regardless of form, and the composition can be applied to control a undesirable plant.

The carrier may be used to provide an environment to support the viability of the microorganism, including by providing the proper environmental conditions and protecting the strain from harmful environmental conditions (e.g., excess oxygen, moisture and/or ultraviolet radiation, etc.). Unless the compositions are generated immediately prior to use, the carrier may be used to maintain the activity of the microorganism during storage (e.g., in a container for the entire shelf-life of the formulated product). The carrier may also be used to maintain the activity of the microorganism after the compositions described throughout have been applied to an application surface (e.g., a plant and/or plant part, in particular, an undesirable plant and/or plant part, and/or a substrate such as a soil). In particular embodiments, the carrier provides an environment such that the microorganism will not have more than a 1-log loss of the original viable content (prior to including in a carrier) over at least a one year period.

In certain embodiments, the compositions described herein may be in the form of a gel, a foam, a solid (such as a powder, granule, particle, etc.), a slurry, or a liquid. In a particular aspect, the composition is in the form of a gel. In another particular aspect, the composition is in the form of a foam. In still another particular aspect, the composition is in the form of a solid (e.g., a powder, granule, particle, etc.). In yet another particular aspect, the composition is in the form of a slurry. In still yet another particular aspect, the composition is in the form of a liquid.

Carrier(s):

The carrier will have the correct values (and range of values) for rheological measurements (e.g., viscosity, yield value, storage modulus, and loss modulus) to allow the one or more strains disclosed herein to remain efficacious (e.g., capable of herbicidal activity) and viable once formulated. Non-limiting examples of carriers described herein include liquids, gels, foams, slurries, or solids (including wettable powders or dry powders).

The selection of the carrier material will depend on the intended application. In a particular embodiment, the carrier is an agronomically acceptable carrier. In a particular aspect, the agronomically acceptable carrier is a foliar-compatible carrier. In another particular aspect, the agronomically acceptable carrier, the carrier is a soil-compatible carrier. In a particular aspect, the agronomically acceptable carrier is a foliar-compatible carrier and a soil compatible carrier.

In a particular embodiment, the carrier is a liquid. In an aspect, the liquid may be an aqueous or non-aqueous liquid carrier. Non-limiting examples of liquids useful as carriers for the compositions disclosed herein include water, an aqueous solution (e.g., sugar water), a non-aqueous liquid, or a non-aqueous solution.

In a particular aspect, the carrier is water. In another aspect the carrier is an aqueous solution. In yet another aspect, the carrier is a non-aqueous liquid.

In a particular aspect, the carrier is a non-aqueous liquid (e.g., an oil, etc.). The non-aqueous liquid may be a biodegradable non-aqueous liquid. The non-aqueous liquid may be a "Low Vapor Pressure Volatile Organic Compounds (LVP-VOC)," which is a chemical "compound" or "mixture of compounds" containing (1) a vapor pressure less than 0.1 mm Hg at 20° C., (2) composed of chemical compounds with more than 12 carbon atoms and/or (3) a boiling point greater than 216° C. See the definition of LVP-VOC provided by the California Air Resources Board (CARB). The non-aqueous liquid may be a biodegradable LVP-VOC non-aqueous liquid.

Non-limiting examples of non-aqueous liquids suitable as a carrier for the compositions described herein include silicone oils, paraffinic/paraffin oils, mineral oils, hexylene glycol, glycerol, linoleic acid, oleic acid, and any combination thereof. Non-limiting examples of a commercial mineral/paraffinic oil include BRITOL 50 (available from Sonneborn, Inc., Mahwah, N.J.), Ultra-Fine Spray oil (available from Sunoco, Petronas Lubricants, Belgium Nev.), SunSpray 6N oil (available from Sunoco, Petronas Lubricants, Belgium Nev.), SunSpray 7E Range oil (available from Sunoco, Petronas Lubricants, Belgium Nev.), SunSpray 7N oil, (available from Sunoco, Petronas Lubricants, Belgium Nev.), SunSpray 11E Range oil (available from Sunoco, Petronas Lubricants, Belgium Nev.), SunSpray 11N oil (available from Sunoco, Petronas Lubricants, Belgium Nev.), Banana Spray oil (available from Sunoco, Petronas Lubricants, Belgium Nev.), and BioSpray oil (available from Sunoco, Petronas Lubricants, Belgium Nev.). An example of a silicone oil is DM Fluid 100 CS (available from Shin-Etsu Chemical Co., Ltd., Tokyo, Japan).

In another embodiment, the carrier is a slurry. In an aspect, the slurry may comprise a sticking agent, a liquid, or a combination thereof. It certain aspects, the sticking agent can be any agent capable of sticking the inoculum (e.g., at least one strain of the microorganisms described herein) to a substrate of interest (e.g., foliage). Non-limiting examples of sticking agents include alginate, mineral oil, syrup, gum arabic, honey, methyl cellulose, milk, wallpaper paste, and combinations thereof. Non-limiting examples of liquids appropriate for a slurry can include water, aqueous solutions, non-aqueous liquids, or non-aqueous solutions.

In another embodiment, the carrier is a solid. In an aspect, the solid is a powder. In one aspect the powder is a wettable powder. In another aspect, the powder is a dry powder. In still another aspect, the solid is a granule. Non-limiting examples of solids useful as carriers for the compositions disclosed herein include peat, wheat, wheat chaff, ground wheat straw, bran, vermiculite, cellulose, starch, soil (pasteurized or unpasteurized), gypsum, talc, clays (e.g., kaolin, bentonite, montmorillonite), and silica gels.

Regardless of the carrier used, in particular aspects, the carrier may further include growth media to culture one or more microorganisms (i.e., microbial strains) which could be useful to the compositions described. Non-limiting examples of suitable growth media for microbial strains include acidified potato dextrose medium (APDA), oatmeal agar (OA), potato dextrose agar, tryptic soy medium, yeast extract mannitol medium (YEM), glycerol yeast extract (GYEA), yeast extract-peptone-glycerol (YPG), peptone yeast extract glucose (PYG) MacConkey agar, or malt extract agar, or in flasks containing suitable liquid media such as tryptic soy broth, YEM broth, KMB broth, GYEA broth. YPG broth, PYG broth, Czapek-Dox medium, potato dextrose broth etc., or any media known to those skilled in the art to be compatible with, and/or provide growth nutrients to the at least one microorganism described herein.

In an embodiment, the composition, may be formed of 1.00 wt. % to 99.99 wt. % of carrier. There may be minor variances when measuring the weight percentage of the carrier and the composition may be formed of about 1.00 wt. % to about 99.99 wt. % of carrier. In particular aspects, the composition may be formed of 50.00 wt. % to 99.99 wt. % of carrier. Again, there may be minor variances when measuring the weight percentage of the carrier and the composition may be formed of about 50.00 wt. % to about 99.99 wt. % of carrier.

Optional Ingredients:

The compositions described herein may comprise one or more optional ingredients that are physically and/or chemically compatible with the composition embodied herein. Non-limiting optional ingredients include agronomically beneficial ingredients (e.g., herbicides, micronutrients, biostimulants, etc.) and additional formulating excipients (e.g., polymers, wetting agents/surfactants, preservatives, antifreezing agents, etc.) and combinations thereof. Such ingredients are known to those skilled in the art.

Agronomically or Agriculturally Beneficial Ingredients:

The compositions disclosed herein may comprise one or more agronomically or agriculturally beneficial ingredients. Non-limiting examples of agronomically beneficial ingredients include herbicides, micronutrients, biostimulants, and combinations thereof.

Herbicides:

In an embodiment, the compositions described herein may comprise at least one herbicide. Alternatively, the at least one herbicide may be applied either simultaneously or applied sequentially, with the compositions disclosed herein.

In a particular aspect, the at least one herbicide may be a pre-emergent herbicide, a post-emergent herbicide, or a combination thereof.

Non-limiting examples of herbicides include acetyl CoA carboxylase (ACCase) inhibitors, acetolactate synthase (ALS) or acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, and nucleic acid inhibitors, salts and esters thereof; racemic mixtures and resolved isomers thereof; and combinations thereof.

In particular aspects, the at least one herbicide is selected from the group consisting of 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluron, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyr-ethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrione, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometryn, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, and haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thenylchlor, tralkoxydim, triclopyr, trietazine, tropramezone, and salts and esters thereof; racemic mixtures and resolved isomers thereof, and combinations thereof.

Micronutrient(s):

In an embodiment, the compositions described herein may comprise one or more micronutrients. Alternatively, the one or more micronutrients may be applied either simultaneously or applied sequentially, with the compositions disclosed herein.

Non-limiting examples of micronutrients for use in the compositions described herein include vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.), macrominerals (e.g., phosphorus, calcium, magnesium, potassium, sodium, iron, etc.), trace minerals (e.g., boron, cobalt, chloride, chromium, copper, fluoride, iodine, iron, manganese, molybdenum, selenium, zinc, etc.), organic acids (e.g., acetic acid, citric acid, lactic acid, malic aclid, taurine, etc.), and combinations thereof. In a particular embodiment, the compositions may comprise phosphorus, boron, chlorine, copper, iron, manganese, molybdenum, zinc or combinations thereof.

In certain embodiments, where the compositions described herein comprise phosphorus, it is envisioned that any suitable phosphorus source may be provided. Non-limiting examples of phosphorus sources include rock phosphate, fertilizers comprising one or more phosphorus sources (e.g., monoammonium phosphate, diammonium phosphate, monocalcium phosphate, super phosphate, triple super phosphate, ammonium polyphosphate, etc.), organic phosphorus sources (e.g., rock powders, seaweed, inoculants, bone meal, meat meal, animal manure, compost, sewage sludge, guano, etc.), and combinations thereof.

Biostimulant(s):

In an embodiment, the compositions described herein may comprise at least one biostimulant. Alternatively, the at least one biostimulant may be applied either simultaneously or applied sequentially, with the compositions disclosed herein.

Biostimulants may enhance metabolic or physiological processes such as respiration, photosynthesis, nucleic acid uptake, ion uptake, nutrient delivery, or a combination thereof. Non-limiting examples of biostimulants include seaweed extracts (e.g., *ascophyllum nodosum*), humic acids (e.g., potassium humate), fulvic acids, myo-inositol, glycine, and combinations thereof. In another embodiment, the compositions comprise seaweed extracts, humic acids, fulvic acids, myo-inositol, glycine, and combinations thereof.

Formulations:

The compositions disclosed herein may be formulated for various applications (e.g., foliar applications, in-furrow applications, drench applications, etc.). The compositions described herein may be formulated with at least one additional formulating excipient to achieve a particular purpose (e.g., for foliar applications, for dilution, etc.).

Additional Formulating Excipients:

Formulations of compositions disclosed herein may further comprise at least one additional formulating excipient. Non-limiting examples of formulating excipients include polymers, wetting agents/surfactants, preservatives, anti-freezing agents, or combinations thereof.

Polymers:

In an embodiment, the formulations of the compositions described herein may comprise at least one polymer.

Non-limiting uses of polymers include agrochemical delivery (e.g., use as an aqueous dispersant), heavy metal removal, water retention and/or water delivery, and combinations thereof. Pouci, et al., Am. J. Agri. & Biol. Sci., 3(1):299-314 (2008). In one embodiment, the one or more polymers is a natural polymer (e.g., agar, starch, alginate, pectin, cellulose, etc.), a synthetic polymer, a biodegradable polymer (e.g., polycaprolactone, polylactide, poly(vinyl alcohol), etc.), or a combination thereof.

For a non-limiting list of polymers useful for the compositions described herein, see Pouci, et al., Am. J. Agri. & Biol. Sci., 3(1):299-314 (2008). In an aspect, the compositions described herein comprise cellulose, cellulose derivatives, methylcellulose, methylcellulose derivatives, starch, agar, alginate, pectin, polyvinylpyrrolidone, polymeric surfactants, and combinations thereof.

Wetting Agents:

In one embodiment, formulations of the compositions described herein may further comprise at least one wetting agent. Wetting agents are commonly used on soils, particularly hydrophobic soils, to improve the infiltration and/or penetration of water into a soil. The wetting agent may be an adjuvant, oil, surfactant, buffer, acidifier, or combination thereof. In an embodiment, the wetting agent is a surfactant. Surfactants suitable as wetting agents for formulating the compositions described herein are provided in the "Surfactants" section.

Surfactants:

Surfactants suitable for formulations of the compositions described herein may be used to wet and/or emulsify soil(s) and/or dirt(s). It is envisioned that the surfactants used for formulating the compositions described herein have low toxicity for any microorganisms contained within the composition. A single surfactant or a blend of several surfactants can be used.

Anionic Surfactants

Anionic surfactants or mixtures of anionic and nonionic surfactants may also be used in formulating the compositions described herein. Anionic surfactants are surfactants having a hydrophilic moiety in an anionic or negatively charged state in aqueous solution. The formulations of the compositions described herein may comprise at least one anionic surfactant. The anionic surfactant(s) may be either water soluble anionic surfactants, water insoluble anionic surfactants, or a combination of water soluble anionic surfactants and water insoluble anionic surfactants. Non-limiting examples of anionic surfactants include sulfonic acids, sulfuric acid esters, carboxylic acids, and salts thereof.

Non-limiting examples of water soluble anionic surfactants include alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, alkyl carboxylates, or a combination thereof.

Nonionic Surfactants

Nonionic surfactants are surfactants having no electrical charge when dissolved or dispersed in an aqueous medium. In at least one aspect of the composition described herein, one or more nonionic surfactants are used as they provide the desired wetting and emulsification actions and do not significantly inhibit spore stability and activity. The nonionic surfactant(s) may be either water soluble nonionic surfactants, water insoluble nonionic surfactants, or a combination of water soluble nonionic surfactants and water insoluble nonionic surfactants.

Water Insoluble Nonionic Surfactants

Non-limiting examples of water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty acid esters, sorbitol ethoxylate esters, or combinations thereof. Also included are EO/PO block copolymers (EO is ethylene oxide, PO is propylene oxide), EO polymers and copolymers, polyamines, and polyvinylpyrrolidones.

Commercially available water insoluble nonionic surfactants that may be suitable for the compositions described herein include Tomadol® 91-2.5, Tomadol® 23-1, Tomadol® 23-3, Span™ 20, Span™ 40, Span™ 60, Span™ 65, Span™ 80, Span™ 85, Arlatone® TV, Atlas® G-1086, Atlas® G-1096, Atlox® 1045A, Cirrasol® G-1086, Cirrasol® G-1096, and combinations thereof.

Water Soluble Nonionic Surfactants

Non-limiting examples of water soluble nonionic surfactants include sorbitan fatty acid alcohol ethoxylates and sorbitan fatty acid ester ethoxylates. I Commercially available water soluble nonionic surfactants that may be suitable for the compositions described herein include Tomadol® 9-11, Tomadol® 23-7, Tomadol® 91-6, Tween® 20, Tween® 21, Tween® 40, Tween® 60, Tween® 80, Surfonic L24-4, and combinations thereof.

Polymeric Surfactants

In particular aspects, the compositions may comprise one or more polymeric surfactants. Polymeric surfactants that may be suitable for the compositions described herein may include one or more nonionic polymeric surfactants, anionic polymeric surfactants, amphoteric polymeric surfactants, cationic polymeric surfactants, and combinations thereof. Particularly useful polymeric surfactants to the compositions described herein are polymeric surfactants that are capable of functioning as an aqueous dispersant.

Nonionic Polymeric Surfactants

Non-limiting examples of nonionic polymeric surfactants include polyalkylene oxide block copolymers, butyl block copolymers, nonionic block copolymers, acrylic copolymer solutions, nonionic random polymeric polymers, polyoxyethylene polyarl phenols, and nonionic polymeric dispersants. Commercially available nonionic polymeric surfactants include, but are not limited to, Atlas® G-5000, Atlas® G-5002L, Atlox® 4894, Atlox® 4912, Atlox® 4912-SF, Atlox® 4913, Atlox® 4914, Cresplus® DP, Hypermer® B206, Hypermer® B210, Hypermer® B246SF, Zyphrym® PD2206, Zyphrym® PD3315, and Zyphrym® PD7000.

Anionic Polymeric Surfactants

Non-limiting examples of anionic polymeric surfactants include styrene acrylic polymers, modified styrene acrylic polymers, and anionic polymeric dispersants. Commercially available anionic polymeric surfactants include, but are not limited to, Atlox® Metasperse 100L, Atlox® Metasperse 500L, Atlox® Metasperse 550S, and Atlox® LP-1.

Polymeric Amphoteric Surfactants

Polymeric amphoteric surfactants suitable for formulating the compositions described herein include, but are not limited to, polymeric amphoteric dispersants. A commercially available polymeric amphoteric dispersant includes, but is not limited to, Atlox® 4915.

Cationic Polymeric Surfactants

Cationic polymeric surfactants suitable for formulating the compositions described herein include, but are not limited to, polyester/polyamine condensation polymers. A commercially available cationic polymeric surfactant includes Hypermer® KD-1.

Other Surfactants

In another embodiment, formulations of the compositions described herein may comprise organosilicone surfactants, silicone-based antifoams used as surfactants in silicone-based and mineral-oil based antifoams. In yet another embodiment, formulations of the compositions described herein may also comprise alkali metal salts of fatty acids (e.g., water soluble alkali metal salts of fatty acids and/or water insoluble alkali metal salts of fatty acids).

Preservatives

In at least one embodiment, the formulations described herein may optionally comprise one or more preservatives. As used herein, the term "preservative" includes a biocide (i.e., a bacteriostats or a bactericides). Non-limiting examples of biocides include the following:

Bactericides:

As used herein, a bactericide is an agent that kills bacteria. A bactericide may be a disinfectant, antiseptic or antibiotic.

Non-limiting examples of a bactericidal disinfectant may be:

active chlorine (i.e., hypochlorites, chloramines, dichloroisocyanurate and trichloroisocyanurate, wet chlorine, chlorine dioxide, etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds, such as chlorhexidine, glucoprotamine, octenidine dihydrochloride, etc.), strong oxidizers, such as ozone and permanganate solutions, heavy metals and their salts, such as colloidal silver, silver nitrate, mercury chloride, phenylmercury salts, copper sulfate, copper oxide-chloride, etc. Heavy metals and their salts are the most toxic, and environment-hazardous bactericides and therefore, their use is strongly oppressed or eliminated, properly concentrated strong acids (phosphoric, nitric, sulfuric, amidosulfuric, toluenesulfonic acids), and alkalis (sodium, potassium, calcium hydroxides), such as of pH<1 or >13, particularly under elevated temperature (above 60° C.), kills bacteria.

Non-limiting examples of a bactericidal antiseptic may be:

properly diluted chlorine preparations (e.g., Daquin's solution, 0.5% sodium or potassium hypochlorite solution, pH-adjusted to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid, some phenolic compounds, such as hexachlorophene, triclosan and Dibromol, and cation-active compounds, such as 0.05-0.5% benzalkonium, 0.5-4% chlorhexidine, 0.1-2% octenidine solutions.

Non-limiting examples of a bactericidal antibiotic may be penicillin, cephalosporins, and aminoglycosidic antibiotics.

Other bactericidal antibiotics include the fluoroquinolones, nitrofurans, vancomycin, monobactams, co-trimoxazole, and metronidazole.

Preferred bactericides are:

A) Halogen containing compounds (e.g., Bronopol—active 2-bromo-2-nitro-1,3-propanadiol; Dowicil 75—active 1-(3-chloroallyl)-3,5,7-triaza-1-azoniaadamantane chloride; DBNPA—active dibromonitrilopropionamide; etc.).

B) OrganoSulfurs—includes Isothaizolones (e.g., Proxel (Nipacide)—active 1,2-benzisothiazolin-3-one; Kathon—active 5-chloro-2-methyl-4-isosthiazolin-3-one, 2-methyl-4-isosthiazolin-3-one; etc.).

C) Nitrogen containing compounds (e.g., Germall II (Diazolidinyl urea); Tris nitro (tris(hydroxymethyl)nitromethane); etc.).

D) Phenolics (e.g., Dowicide (sodium o-phenylphenate); Preventol D2® (benzyl-hemiformal); etc.).

E) Inorganics (e.g., copper arsenates; cuprous oxide; etc.).

F) Organometallics (e.g., compounds of arsenic, copper, mercury, etc.).

G) Quaternary ammonium compounds.

Bacteriostats:

As used herein, a bacteriostat is an agent, usually chemical, that prevents the growth of bacteria but that does not necessarily kill them or their spores. Upon removal of the bacteriostat, the bacteria usually start to grow again.

Non-limiting examples of bacteriostats include sodium azide and thimerosol.

Anti-Freezing Agent(s):

In particular aspects, the formulations described herein may further comprise one or more anti-freezing agents. Non-limiting examples of anti-freezing agents include ethylene glycol, propylene glycol, urea, glycerin, and combinations thereof.

Methods

Further disclosed are methods for controlling at least one plant, such as an undesirable plant, comprising using the disclosed strains, including variants thereof, as well as suspensions or whole cell broths comprising the strains disclosed herein, or a supernatant, filtrate, or extract derived from any of the strains disclosed herein, suspensions or whole cell broths in such methods. In another aspect, methods for controlling at least one plant (e.g., an undesirable plant) comprise using the compositions and formulations described herein.

In particular, the methods described herein are potentially useful for controlling at least one plant from the genus *Toxicodendron* spp. (e.g., *Toxicodendron acuminatum, Toxicodendron diversilobum* (i.e., Western poison oak), *Toxicodendron orientale* (i.e., Asian poison ivy), *Toxicodendron parviflorum, Toxicodendron potaninii* (i.e., Potanin's lacquer tree, also referred to as the Chinese varnish tree), *Toxicodendron pubescens* (i.e., Atlantic poison oak), *Toxicodendron radicans* (i.e., Poison ivy), *Toxicodendron rydbergii* (i.e., Western poison ivy), *Toxicodendron striatum* (i.e., Manzanillo), *Toxicodendron succedaneum* (i.e., Wax tree), *Toxicodendron sylvestre, Toxicodendron vernicifluum* (i.e., Japanese lacquer tree or Japanese varnish tree), and *Toxicodendron vernix* (i.e., Poison sumac)) and *Schinus* spp. (e.g., *Schinus engleri, Schinus latifolius, Schinus lentiscifolius, Schinus molle* (i.e., Peruvian Pepper Tree), *Schinus pearcei, Schinus polygamus, Schinus terebinthifolius* (i.e., Brazilian Pepper Tree, also referred to as Aroeira, Rose Pepper, and Christmasberry), *Schinus, venture*, and *Schinus weinmanniifolius*).

In still a more particular aspect, the methods described herein control *Toxicodendron diversilobum* (i.e., Western poison oak). In still yet a more particular aspect, the methods described herein control *Toxicodendron pubescens* (i.e., Atlantic poison oak). In still an even more particular aspect, the methods described herein control *Toxicodendron radicans* (i.e., Poison ivy). In still another particular aspect, the methods described herein control *Toxicodendron rydbergii* (i.e., Western poison ivy). In still yet another particular aspect, the methods described herein control *Toxicodendron vernix* (i.e., Poison sumac). In still yet another particular aspect, the methods described herein control *Schinus terebinthifolius* (i.e., Brazilian pepper tree, also referred to as, Aroeira, Rose Pepper, and Christmasberry).

In one embodiment, the method of controlling at least one undesirable plant comprises contacting at least one undesirable plant or plant part with at least one strain of *Colletotrichum* spp., e.g., *Colletotrichum acutatum, Colletotrichum agaves, Colletotrichum alcornii, Colletotrichum arachidis, Colletotrichum baltimorense, Colletotrichum capsici, Colletotrichum caudatum, Colletotrichum cereale, Colletotrichum coccodes, Colletotrichum crassipes, Colletotrichum dematium, Colletotrichum derridis, Colletotrichum destructivum, Colletotrichum falcatum, Colletotrichum fioriniae, Colletotrichum fragariae, Colletotrichum gloeosporioides, Colletotrichum gossypii, Colletotrichum graminicola, Colletotrichum hanaui, Colletotrichum higginsianum, Colletotrichum jacksonii, Colletotrichum kahawae, Colletotrichum lindemuthianum, Colletotrichum lini, Colletotrichum mangenotii, Colletotrichum musae, Colletotrichum navitas, Colletotrichum nicholsonii, Colletotrichum nigrum, Colletotrichum orbiculare, Colletotrichum paspali, Colletotrichum pisi, Colletotrichum somersetense, Colletotrichum sublineolum, Colletotrichum trichellum, Colletotrichum trifolii, Colletotrichum truncatum, Colletotrichum viniferum, Colletotrichum zoysiae*, and combinations thereof.

In one aspect, the method of controlling at least one undesirable plant comprises contacting at least one undesirable plant or plant part with at least one strain of *Colletotrichum fioriniae*. In a more particular aspect, the method of controlling at least one undesirable plant comprises contacting at least one undesirable plant or plant part with at least one strain of *Colletotrichum fioriniae* selected from the group consisting of *Colletotrichum fioriniae* strain TR-123, *Colletotrichum fioriniae* strain TR-126, and combinations thereof. In still a more particular aspect, the method of controlling at least one undesirable plant comprises contacting at least one undesirable plant or plant part with *Colletotrichum fioriniae* strain TR-123. In yet a more particular aspect, the method of controlling at least one undesirable plant comprises contacting at least one undesirable plant or plant part with *Colletotrichum fioriniae* strain TR-126. In still yet a more particular aspect, the method of controlling at least one undesirable plant comprises contacting at least one undesirable plant or plant part with a mixture of *Colletotrichum fioriniae* strain TR-123 and *Colletotrichum fioriniae* strain TR-126.

In another aspect, the method of controlling at least one undesirable plant comprises contacting at least one undesirable plant or plant part with an effective amount of at least one strain of *Colletotrichum fioriniae* to control the undesirable plant. In a more particular aspect, the method of controlling at least one undesirable plant comprises contacting at least one undesirable plant or plant part with an effective amount of at least one strain of *Colletotrichum fioriniae* to control the undesirable plant selected from the group consisting of *Colletotrichum fioriniae* strain TR-123, *Colletotrichum fioriniae* strain TR-126, and combinations thereof. In still a more particular aspect, the method of controlling at least one undesirable plant comprises contacting at least one undesirable plant or plant part with an effective amount of *Colletotrichum fioriniae* strain TR-123 to control the undesirable plant. In yet a more particular aspect, the method of controlling at least one undesirable plant comprises contacting at least one undesirable plant or plant part with an effective amount of *Colletotrichum fioriniae* strain TR-126 to control the undesirable plant. In still yet a more particular aspect, the method of controlling at least one undesirable plant comprises contacting at least one undesirable plant or plant part with an effective amount of a mixture of *Colletotrichum fioriniae* strain TR-123 and *Colletotrichum fioriniae* strain TR-126 to control the undesirable plant.

In another aspect, the method of controlling at least one undesirable plant comprises contacting at least one undesirable plant or plant part with at least one of the compositions described herein. In a more particular aspect, the method of controlling at least one undesirable plant comprises contacting at least one undesirable plant or plant part with an effective amount of at least one of the compositions described herein to control the undesirable plant. In an even more particular aspect, the compositions are formulated with at least one formulating excipient as described herein.

Contacting at least one plant or plant part with at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation described herein may be performed according to methods known to those skilled in the art.

Non-limiting examples of contacting at least one undesirable plant or plant part with at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation described herein include foliar contact (e.g., spraying or dusting the at least one strain, composition, or formulation described herein onto the at least one plant or plant part), in-furrow contact, etc.

In a particular aspect, the contacting step comprises foliarly applying the at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation described herein to at least one undesirable plant or plant part.

In another particular aspect, the contacting step comprises spraying the at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation described herein to at least one undesirable plant or plant part.

In still another particular aspect, the contacting step comprises dusting the at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation described herein to at least one undesirable plant or plant part.

In still yet another particular aspect, the contacting step comprises in-furrow contact with at least one undesirable plant or plant part with at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation as described herein.

In another embodiment, the method of controlling at least one undesirable plant comprises contacting a substrate (e.g., a soil) for at least one undesirable plant with at least one strain of *Colletotrichum* spp., e.g., *Colletotrichum acutatum, Colletotrichum agaves, Colletotrichum alcornii, Colletotrichum arachidis, Colletotrichum baltimorense, Colletotrichum capsici, Colletotrichum caudatum, Colletotrichum cereale, Colletotrichum coccodes, Colletotrichum crassipes, Colletotrichum dematium, Colletotrichum derridis, Colletotrichum destructivum, Colletotrichum falcatum, Colletotrichum fioriniae, Colletotrichum fragariae, Colletotrichum gloeosporioides, Colletotrichum gossypii, Colletotrichum graminicola, Colletotrichum hanaui, Colletotrichum higginsianum, Colletotrichum jacksonii, Colletotrichum kahawae, Colletotrichum lindemuthianum, Colletotrichum lini, Colletotrichum mangenotii, Colletotrichum musae, Colletotrichum navitas, Colletotrichum nicholsonii, Colletotrichum nigrum, Colletotrichum orbiculare, Colletotrichum paspali, Colletotrichum pisi, Colletotrichum somersetense, Colletotrichum sublineolum, Colletotrichum trichellum, Colletotrichum trifolii, Colletotrichum truncatum, Colletotrichum viniferum, Colletotrichum zoysiae*, and combinations thereof.

In an aspect, the method of controlling at least one undesirable plant comprises contacting a substrate (e.g., a soil) for at least one undesirable plant with at least one strain of *Colletotrichum fioriniae*. In a more particular aspect, the method of controlling at least one undesirable plant comprises contacting a substrate (e.g., a soil) for at least one undesirable plant with at least one strain of *Colletotrichum fioriniae* selected from the group consisting of *Colletotrichum fioriniae* strain TR-123, *Colletotrichum fioriniae* strain TR-126, and combinations thereof. In still a more particular aspect, the method of controlling at least one undesirable plant comprises contacting a substrate (e.g., a soil) for at least one undesirable plant with *Colletotrichum fioriniae* strain TR-123. In yet a more particular aspect, the method of controlling at least one undesirable plant comprises contacting a substrate (e.g., a soil) for at least one undesirable plant with *Colletotrichum fioriniae* strain TR-126. In still yet a more particular aspect, the method of controlling at least one undesirable plant comprises contacting a substrate (e.g., a soil) for at least one undesirable plant with a mixture of *Colletotrichum fioriniae* strain TR-123 and *Colletotrichum fioriniae* strain TR-126.

In another aspect, the method of controlling at least one undesirable plant comprises contacting a substrate (e.g., a soil) for at least one undesirable plant with an effective amount of at least one strain of *Colletotrichum fioriniae* to control the undesirable plant. In a more particular aspect, the method of controlling at least one undesirable plant comprises contacting a substrate (e.g., a soil) for at least one undesirable plant with an effective amount of at least one strain of *Colletotrichum* fioriniae selected from the group consisting of *Colletotrichum fioriniae* strain TR-123, *Colletotrichum fioriniae* strain TR-126, and combinations thereof to control the undesirable plant. In still a more particular aspect, the method of controlling at least one undesirable plant comprises contacting a substrate (e.g., a soil) for at least one undesirable plant with an effective amount of *Colletotrichum fioriniae* strain TR-123 to control the undesirable plant. In yet a more particular aspect, the method of controlling at least one undesirable plant comprises contacting a substrate (e.g., a soil) for at least one undesirable plant with an effective amount of *Colletotrichum fioriniae* strain TR-126 to control the undesirable plant. In still yet a more particular aspect, the method of controlling at least one undesirable plant comprises contacting a substrate (e.g., a soil) for at least one undesirable plant with an effective amount of a mixture of *Colletotrichum fioriniae* strain TR-123 and *Colletotrichum fioriniae* strain TR-126 to control the undesirable plant.

In another aspect, the method of controlling at least one undesirable plant comprises contacting a substrate (e.g., a soil) for at least one undesirable plant with at least one of the compositions described herein. In a more particular aspect, the method of controlling at least one undesirable plant comprises contacting a substrate (e.g., a soil) for at least one undesirable plant with an effective amount of at least one of the compositions described herein to control the undesirable plant. In one aspect, the compositions are formulated with at least one formulating excipient.

Contacting a substrate (e.g., a soil) with at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation described herein may be performed according to methods known to those skilled in the art.

Non-limiting examples of contacting a substrate (e.g., a soil) with at least one *Colletotrichum* spp. strain (e.g., *Colletotrichum fioriniae*, and in particular, *Colletotrichum fioriniae* strain TR-123, *Colletotrichum fioriniae* strain TR-126, and combinations thereof) or at least one composition or formulation described herein include foliar contact (e.g., spraying or dusting, etc.), in-furrow contact, coating seeds, etc. as described above.

EXAMPLES

The following examples are provided for illustrative purposes and are not intended to limit the scope of the invention as claimed herein. Any variations in the exemplified examples which occur to the skilled artisan are intended to fall within the scope of the present invention.

Biological Deposits

NRRL is the abbreviation for the Agricultural Research Culture Collection, an international depositary authority for the purposes of depositing microorganism strains under the Budapest Treaty on the international recognition of the deposit of microorganisms for the purpose of patent procedure.

Deposits, intended to meet all requirements of 37 C.F.R. §§1.801-1.809, of *Colletotrichum fioriniae* TR-123 and *Colletotrichum fioriniae* TR-126 disclosed above were made under the provisions of the Budapest Treaty with the Agricultural Research Culture Collection (NRRL), International Depositary Authority, 1815 N. University Street, Peoria, Ill. 61604 USA. The desposits were accepted and assigned the following accession numbers provided in Table 1:

TABLE 1

Deposited Strains:

| Identification | Accession Number | Date of Deposit |
|---|---|---|
| *Colletotrichum fioriniae* TR-123 | NRRL 50987 | Nov. 7, 2014 |
| *Colletotrichum fioriniae* TR-126 | NRRL 50988 | Nov. 7, 2014 |

Example 1

Isolation of *Colletotrichum* Strains

Poison ivy (*Toxicodendron radicans*) drupes were collected from solitary lianas in Roanoke and Montgomery Counties, Virginia. These drupes were subjected to experiments aimed at producing sterile seedlings (Benhase, E. and Jelesko, J., HortSci., 48:1, 2013); however, there was extensive blighting and wilting in the germinated seedlings.

Associated with the drupes and seedlings was a fungus with white to pale olivaceous grey mycelium with orange blister-like conidiomata and sclerotial masses enclosing the drupe mesocarp as well as conidiomata emerging from blighted, necrotic leaves. Condiomata were plated onto acidified potato dextrose agar (APDA) and Oatmeal Agar (OA). This consistently yielded colonies identical to those described from diseased tissues and were putatively identified as *Colletotrichum acutatum* based on the presence of acervuli containing hyaline, smooth-walled, aseptate conidia with acute ends; the absence of setae; and formation of red pigments in culture. (Damm, U. et al., Stud. Mycol., 73:37, 2012).

Conidial dimensions of four isolates most closely aligned with reported measurements for *Colletotrichum fioriniae* (Shivas, R. et al., Fungal Divers., 39:111): mean length±SD×width±SD=15.1±1.7×4.9±0.3 μm, L/W ratio=3.04 on OA.

Fungal DNA of two *Colletotrichum fioriniae* isolates, TR-123 and TR-126, was isolated and used as template in PCR reactions using oligonucleotide primer pairs corresponding to the internal transcribed spacer (ITS) region, and a portion of the glyceraldehyde-3-phosphate dehydrogenase (GAPDH) genes.

Conditions for PCR included an initial denaturation step of 5 min at 94° C., followed by 40 cycles of 30 s at 94° C., 30 s at 52° C. and 30 s at 72° C., and a final denaturation step of 7 min at 72° C., while the ITS PCR was performed as described by Woudenberg, J. H. C. et al., *Persoonia,* 22:56, 2009.

The resulting PCR fragments were sequenced and used as queries in BLASTN searches of the Genbank NR database:

ITS Sequences:

TR-123 (ITS corresponding to SEQ ID NO: 1) and

TR-126 (ITS corresponding to SEQ ID NO: 2).

GAPDH Sequences:

TR-123 (GAPDH corresponding to SEQ ID NO: 3) and

TR-126 (GAPDH corresponding to SEQ ID NO: 4).

All of the amplified ITS DNA sequences (497 bps) (SEQ ID NO. 1 and 2) were identical to *Glomerella/Colletotrichum fioriniae* (GenBank JN121190 and KF278459), with no gaps in the multiple sequence alignment.

Similarly, the amplified (672 bps) GAPDH sequences (SEQ ID NO. 3 and 4) were 99.6% similar over the 254 bps overlapping with *C. fioriniae* (GenBank JQ948622) with no gaps in the multiple sequence alignment.

Example 2

Efficacy of *Colletotrichum* Against Poison Ivy

Pathogenicity of two *C. fioriniae* isolates, TR-123 and TR-126, was confirmed by placing 4.75 mm dia. inoculated agar plugs from 8-day-old fungal cultures or a sterile plug (negative control) at the base of an axenic young poison ivy seedlings ca. 1.5-6.5 cm in height with at least one set of true leaves. (Benhase, E. and Jelesko, J., HortSci., 48:1, 2013). Each treatment was replicated five times. Disease progression among treatments on poison ivy. Treatments with significantly different Area Under the Disease Progress Curve means are indicated by different letters, as determined by ANOVA with Tukey's mean comparisons using Minitab 16.1.0. Disease ratings were: 1=healthy, 2=chlorotic leaves, 3=wilt/necrosis, and 4=dead. Results are provided in FIG. 1.

As shown in FIGS. 2A-2F, acute wilt and blighting of leaves and production of orange acervuli on cotyledons disease symptoms developed by three weeks post inoculation (WPI). By seven WPI all but one of the *Colletotrichum*-inoculated plants were dead, whereas all of the control plants were healthy with significantly lower Area Under the Disease Progress Curve values. FIGS. 2A-2F show the effect of *C. fioriniae* isolate TR-126 on *Toxicodendron radicans* after 3 weeks when compared to the control.

*Colletotrichum* was consistently re-isolated, and confirmed morphologically and molecularly, from six of seven diseased seedlings, whereas two of two randomly chosen control seedlings remained asymptomatic and did not yield *Colletotrichum.*

Example 3

Efficacy of *Colletotrichum* Against Brazilian Pepper Tree

Pathogenicity of *C. fioriniae* isolate, TR-123, against *Schinus terebinthifolus* (Brazilian Pepper Tree) was confirmed according to the methods of Example 2. As shown in FIG. 3A, four week old Brazilian peppertree seedlings inoculated with a sterile agar plug (negative control) and *C. fioriniae* isolate TR-123 (right) at the base of the seedling. FIGS. 3B-3C show *C. fioriniae* isolate TR-123 infected plants. In particular, FIGS. 3B-3C show that plants infected with isolate TR-123 demonstrate wilt symptoms leaf blight, leaf tip discoloration and necrosis on green terminal leaves, and orange acervuli of *C. fioriniae* on necrotic leaves.

It will be understood that the Specification and Examples are illustrative of the present embodiments and that other embodiments within the spirit and scope of the claimed embodiments will suggest themselves to those skilled in the art. Although this disclosure has been described in connection with specific forms and embodiments thereof, it would be appreciated that various modifications other than those discussed above may be resorted to without departing from the spirit or scope of the embodiments as defined in the appended claims. For example, equivalents may be substituted for those specifically described, and in certain cases, particular applications of steps may be reversed or interposed all without departing from the spirit or scope for the disclosed embodiments as described in the appended claims. Additionally, one skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of controlling at least one plant, comprising contacting at least one plant or plant part with at least one strain of *Colletotrichum fioriniae*, wherein the plant is a plant selected from the group consisting of *Toxicodendron acuminatum, Toxicodendron diversilobum, Toxicodendron orientale, Toxicodendron parviflorum, Toxicodendron potaninii, Toxicodendron pubescens, Toxicodendron radicans, Toxicodendron rydbergii, Toxicodendron striatum, Toxicodendron succedaneum, Toxicodendron sylvestre, Toxicodendron vernicifluum, Toxicodendron vernix, Schinus engleri, Schinus latifolius, Schinus lentiscifolius, Schinus molle, Schinus pearcei, Schinus polygamus, Schinus terebinthifolius, Schinus venture, Schinus weinmanniifolius*, and combinations thereof.

2. The method of claim 1, wherein the at least one strain of *Colletotrichum fioriniae* is selected from the group consisting of *Colletotrichum fioriniae* TR-123, *Colletotrichum fioriniae* TR-126, and combinations thereof.

3. The method of claim 1, wherein the method further comprises contacting at least one plant or plant part with at least one herbicide.

4. The method of claim 3, wherein the at least one herbicide is selected from the group consisting of acetyl CoA carboxylase (ACCase) inhibitors, acetolactate synthase (ALS) or acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors, and combinations thereof.

5. The method of claim 3, wherein the at least one herbicide is selected from the group consisting of 2,4-dichlorophenoxyacetic acid (2,4-0), 2,4,5trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluron, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyr-ethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrione, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometryn, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifopP-butyl, haloxyfop-methyl, and haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thenylchlor, tralkoxydim, triclopyr, trietazine, tropramezone, and combinations thereof.

6. The method of claim 1, wherein the plant is *Toxicodendron radicans*.

7. The method of claim 1, wherein the plant is *Schinus terebinthifolus*.

8. A method of controlling at least one plant of the genus *Toxicodendron*, comprising contacting at least one plant of the genus *Toxicodendron* or plant part thereof with an effective amount of at least one strain of *Colletotrichum fioriniae*.

9. The method of claim 8, wherein the at least one strain of *Colletotrichum fioriniae* is selected from the group consisting of *Colletotrichum fioriniae* TR-123, *Colletotrichum fioriniae* TR-126, and combinations thereof.

10. The method of claim 8, wherein the method further comprises contacting the at least one plant of the genus *Toxicodendron* or plant part thereof with at least one herbicide.

11. The method of claim 10, wherein the at least one herbicide is selected from the group consisting of acetyl CoA carboxylase (ACCase) inhibitors, acetolactate synthase (ALS) or acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors, and combinations thereof.

12. The method of claim 10, wherein the at least one herbicide is selected from the group consisting of 2,4-dichlorophenoxyacetic acid (2,4-0), 2,4,5trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluron, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyr-ethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrione, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometryn, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifopP-butyl, haloxyfop-methyl, and haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thenylchlor, tralkoxydim, triclopyr, trietazine, tropramezone, and combinations thereof.

13. The method of claim 8, wherein the plant is *Toxicodendron radicans*.

14. A method of controlling at least one plant of the genus *Schinus*, comprising contacting at least one plant of the genus *Schinus* or plant part thereof with an effective amount of at least one strain of *Colletotrichum fioriniae*.

15. The method of claim 14, wherein the at least one strain of *Colletotrichum fioriniae* is selected from the group consisting of *Colletotrichum fioriniae* TR-123, *Colletotrichum fioriniae* TR-126, and combinations thereof.

16. The method of claim 14, wherein the method further comprises contacting the at least one plant of the genus *Schinus* or plant part thereof with at least one herbicide.

17. The method of claim 16, wherein the at least one herbicide is selected from the group consisting of acetyl CoA carboxylase (ACCase) inhibitors, acetolactate synthase (ALS) or acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors, and combinations thereof.

18. The method of claim 16, wherein the at least one herbicide is selected from the group consisting of 2,4-dichlorophenoxyacetic acid (2,4-0), 2,4,5trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluron, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyr-ethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrione, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometryn, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifopP-butyl, haloxyfop-methyl, and haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thenylchlor, tralkoxydim, triclopyr, trietazine, tropramezone, and combinations thereof.

19. The method of claim 14, wherein the plant is *Schinus terebinthifolus*.

* * * * *

SEQUENCE LISTING

```
<160> NUMBER OF SEQ ID NOS: 4

<210> SEQ ID NO 1
<211> LENGTH: 497
<212> TYPE: DNA
<213> ORGANISM: Colletotrichum fioriniae
<220> FEATURE:
<221> NAME/KEY: misc_feature
<223> OTHER INFORMATION: TR-123 Internal Transcribed Spacer Region (ITS)

<400> SEQUENCE: 1

atcattactg agttaccgct ctataaccct ttgtgaacgt acctaaccgt tgcttcggcg     60

ggcaggggaa gcctctcgcg ggcctcccct cccggcgccg gcccccacca cggggacggg    120

gcgcccgccg gaggaaacca aactctattt acacgacgtc tcttctgagt ggcacaagca    180

aataattaaa acttttaaca acggatctct tggttctggc atcgatgaag aacgcagcga    240

aatgcgataa gtaatgtgaa ttgcagaatt cagtgaatca tcgaatcttt gaacgcacat    300

tgcgctcgcc agcattctgg cgagcatgcc tgttcgagcg tcatttcaac cctcaagcac    360

cgcttggttt tggggcccca cggccgacgt gggcccttaa aggtagtggc ggaccctccc    420

ggagcctcct ttgcgtagta actaacgtct cgcactggga tccggaggga ctcttgccgt    480

taaacccccca aattctt                                                  497


<210> SEQ ID NO 2
<211> LENGTH: 497
<212> TYPE: DNA
<213> ORGANISM: Colletotrichum fioriniae
<220> FEATURE:
<221> NAME/KEY: misc_feature
<223> OTHER INFORMATION: TR-126 Internal Transcribed Spacer Region (ITS)

<400> SEQUENCE: 2

atcattactg agttaccgct ctataaccct ttgtgaacgt acctaaccgt tgcttcggcg     60

ggcaggggaa gcctctcgcg ggcctcccct cccggcgccg gcccccacca cggggacggg    120

gcgcccgccg gaggaaacca aactctattt acacgacgtc tcttctgagt ggcacaagca    180

aataattaaa acttttaaca acggatctct tggttctggc atcgatgaag aacgcagcga    240

aatgcgataa gtaatgtgaa ttgcagaatt cagtgaatca tcgaatcttt gaacgcacat    300

tgcgctcgcc agcattctgg cgagcatgcc tgttcgagcg tcatttcaac cctcaagcac    360

cgcttggttt tggggcccca cggccgacgt gggcccttaa aggtagtggc ggaccctccc    420

ggagcctcct ttgcgtagta actaacgtct cgcactggga tccggaggga ctcttgccgt    480

taaacccccca aattctt                                                  497


<210> SEQ ID NO 3
<211> LENGTH: 672
<212> TYPE: DNA
<213> ORGANISM: Colletotrichum fioriniae
<220> FEATURE:
<221> NAME/KEY: misc_feature
<223> OTHER INFORMATION: TR-123 Glyceraldehyde-3-Phosphate Dehydrogenase
      Genes (GAPDH)

<400> SEQUENCE: 3

tcgagatcgt tgccgtcacg accctttcat tgagaccaag tacgctgtga gtatcacccc     60

cactttaccc ctccataatg atatcacgtc tgctacaata acaccagctt catcggtaac    120

cacgggaaaa gagtcagagc tagtactctc gactctttgg acccaaggtt tcgattgggc    180

tcgttgttgt aatgatacga cgtgacacaa tcatgcagaa acagcccaaa caaaatttgc    240
```

-continued

```
tgacagacaa tcatcacagg cctacatgct caagtacgac tccacccacg gcatcttcaa    300

cggcgacatc cagcaggatg gcaacgacct tgtcatcaac ggcaagaagg tcaagttcta    360

cactgagcgt gaccccgctg ccatcccctg gaaggacacc ggcgccgact acgtcgtcga    420

gtccactggt gtcttcacca ccatcgacaa ggcgaaggcc catctccagg gcggtgccaa    480

gaaggtcgtc atctctgctc cctctgccga tgcccccatg tacgtgatgg gtgtcaacga    540

gaagacctac gacggcagcg ccgacgttat ctccaacgct tcttgcacca ccaactgcct    600

ggctcccctc gccaaggtca tcaacgacaa gttcaccatc attgagggtc tcatgaccac    660

cgtccactcc ta                                                        672


<210> SEQ ID NO 4
<211> LENGTH: 672
<212> TYPE: DNA
<213> ORGANISM: Colletotrichum fioriniae
<220> FEATURE:
<221> NAME/KEY: misc_feature
<223> OTHER INFORMATION: TR-126 Glyceraldehyde-3-Phosphate Dehydrogenase
      Genes (GAPDH)

<400> SEQUENCE: 4

tcgagatcgt tgccgtcacg accctttcat tgagaccaag tacgctgtga gtatcacccc     60

cactttaccc ctccataatg atatcacgtc tgctacaata acaccagctt catcggtaac    120

cacgggaaaa gagtcagagc tagtactctc gactctttgg acccaaggtt tcgattgggc    180

tcgttgttgt aatgatacga cgtgacacaa tcatgcagaa acagcccaaa caaaatttgc    240

tgacagacaa tcatcacagg cctacatgct caagtacgac tccacccacg gcatcttcaa    300

cggcgacatc cagcaggatg gcaacgacct tgtcatcaac ggcaagaagg tcaagttcta    360

cactgagcgt gaccccgctg ccatcccctg gaaggacacc ggcgccgact acgtcgtcga    420

gtccactggt gtcttcacca ccatcgacaa ggcgaaggcc catctccagg gcggtgccaa    480

gaaggtcgtc atctctgctc cctctgccga tgcccccatg tacgtgatgg gtgtcaacga    540

gaagacctac gacggcagcg ccgacgttat ctccaacgct tcttgcacca ccaactgcct    600

ggctcccctc gccaaggtca tcaacgacaa gttcaccatc attgagggtc tcatgaccac    660

cgtccactcc ta                                                        672
```